United States Patent [19]  [11] 4,057,591
Ozawa et al.  [45] Nov. 8, 1977

[54] PROCESS FOR PREPARING OLIGOMERS OF TETRAFLUOROETHYLENE

[75] Inventors: Masahiro Ozawa; Fumio Inoue, both of Kamifukuoka; Tadaaki Komatsu, Saitama; Kimiaki Matsuoka, Kawagoe, all of Japan

[73] Assignee: Central Glass Company, Limited, Ube, Japan

[21] Appl. No.: 696,718

[22] Filed: June 16, 1976

[30] Foreign Application Priority Data

June 16, 1975 Japan .................................. 50-72054

[51] Int. Cl.$^2$ ....................... C07C 21/18; C08F 2/38; C07C 17/26
[52] U.S. Cl. ............................................. 260/653.1 R
[58] Field of Search ................................. 260/653.1 R

[56] References Cited

U.S. PATENT DOCUMENTS

| | | | |
|---|---|---|---|
| 3,403,191 | 9/1968 | Graham | 260/653.1 R |
| 3,917,724 | 11/1975 | Martini | 260/653.1 R |
| 3,983,179 | 9/1976 | Riess et al. | 260/653.1 R X |

Primary Examiner—Delbert E. Gantz
Assistant Examiner—Joan Thierstein
Attorney, Agent, or Firm—Fleit & Jacobson

[57] ABSTRACT

Oligomers of tetrafluoroethylene are prepared by oligomerization of tetrafluoroethylene in an organic solvent in the presence of a fluoride compound and a crown ether. The catalytic action of the fluoride compound can be far improved when the fluoride compound is used together with a crown ether.

19 Claims, No Drawings

PROCESS FOR PREPARING OLIGOMERS OF TETRAFLUOROETHYLENE

This invention relates to a process for preparing oligomers of tetrafluoroethylene.

Oligomers of tetrafluoroethylene, particularly oligomers having 4 or more carbon atoms, are known to be useful as media or solvents under high temperature conditions or as starting materials for water or oil repellants and various kinds of industrial surfactants, as well as oligomers of hexafluoropropene.

In general, oligomers of tetrafluoroethylene can be produced by catalytically treating tetrafluoroethylene monomer with various kinds of fluoride anion sources in non-protolytic solvents. For example, U.S. Pat. No. 3403191 describes a process for the preparation of tetrafluoroethylene oligomers using a CsF catalyst and a diglyme solvent, and Japanese Patent Publication No. 11885/1968 describes a process using a catalyst under water-free conditions at least one fluoride selected from fluorides, acid metal fluorides and quaternary ammonium fluorides of K, Rb and Cs. Further, Japanese Patent Publication No. 22563/1972 teaches use as a catalyst of quaternary ammonium fluoride prepared from a quaternary ammonium halide (exclusive of fluoride) and KF. In the above specifications it is described that use of CsF or quaternary ammonium fluoride is particularly effective in producing good oligomerization results. However, the use of CsF or quaternary ammonium fluoride is disadvantageous from a viewpoint of industrial production of the oligomers in that the compounds are expensive, that it takes a long period of time in preparing such compounds, and that it is difficult to handle because of high hygroscopicity of the compounds. In contrast, use of other fluoride or the acid metal fluorides is also disadvantageous in that the oligomerization reaction must be effected under relatively severe reaction conditions, with relatively low yield of oligomers. Accordingly, there is a strong demand for a process for the preparation of oligomers of tetrafluoroethylene using an inexpensive and easy-to-handle catalyst with excellent catalytic activity.

It is therefore an object of the present invention to provide an improved process for preparing oligomers of tetrafluoroethylene which overcomes the disadvantages of the prior processes.

It is another object of the present invention to provide a process for oligomerizing tetrafluoroethylene under mild reaction conditions to produce branched perfluoroolefins having 4 or more carbon atoms in high yield.

It is a further object of the present invention to provide a process for preparing oligomers of tetrafluoroethylene in high yield by using as one component of catalyst a fluoride compound, particularly potassium fluoride, which is inexpensive and easy to handle.

The above objects can be attained by subjecting tetrafluoroethylene monomer to an oligomerization reaction in an organic solvent in the presence of a fluoride compound and a crown ether. It has been found that the catalytic action of the fluoride compound on the oligomerization reaction is far improved when the fluoride compound is used in combination with a crown ether. Further, perfluoroolefins having 4 or more carbon atoms, particularly pentamer, having a variety of applications can be produced in high selectivity.

Examples of suitable fluoride compounds used in combination with a crown ether are metal fluorides, particularly alkali metal fluorides such as potassium fluoride, sodium fluoride, cesium fluoride, etc., ammonium fluoride, quaternary ammonium fluoride, etc. Of these, potassium fluoride and sodium fluoride are used preferably, and most preferably potassium fluoride because of economy and easiness of preparation thereof.

These fluoride compounds and crown ethers are sufficient to be used only in catalytic amounts. The fluoride compound and crown ether readily form a complex salt which is considered to serve as the catalyst for tetrafluoroethylene. It is assumed that upon formation of a complex salt with a fluoride compound, the crown ether exerts a strong trapping action (or coordination action) on cations, e.g., potassium ions or ammonium ions, of the fluoride compound, taking the cations in its holes.

This assists in accelerating the dissociation of corresponding anions of the fluoride to impart to the anions a considerably increased nucleophilic ability. Accordingly, the choice of a crown ether should preferably depend on the kind of the fluoride compound so that the chosen crown ether has a diameter of holes sufficient for receiving cations of the fluoride compound.

The term "crown ether" used herein is understood to imply all of macrocyclic ethers (oxygen of which may be at least partially substituted with nitrogen, sulfur or phosphorus) which have functions of aggressively coordinating cations within its holes and of activating corresponding anions in a catalytic sense. The macrocyclic ethers are, for example, a group of cyclic polyethers as defined by C. J. Pedersen in the Journal of the American Chemical Society (89, pages 7017–7036, 1967) which are incorporated herein by reference. Examples of the crown ethers suitable for the practice of the invention include, according to a simplified nomenclature by C. J. Pedersen et al, decalyl-15-crown-5, dibenzo-14-crown-4, dibenzo-20-crown-4, dibenzo-18-crown-5, asym-dibenzo-19-crown-6, 18-crown-6, dibenzo-18-crown-6, dicyclohexyl-18-crown-6, asym-dicyclohexyl-48-crown-16, asym-dibenzo-22-crown-6, dibenzo-26-crown-6, etc., and compounds obtained by substituting a part or all of oxygen atoms of the above-indicated cyclic polyethers with sulfur atoms. Of these, 18-crown-6 compounds including 18-crown-6, dibenzo-18-crown-6 and dicyclohexyl-18-crown-6 are preferred since they are easy to prepare. Further, there may be also used another type of crown ether compounds or cryptate compounds expressed by the following general formula

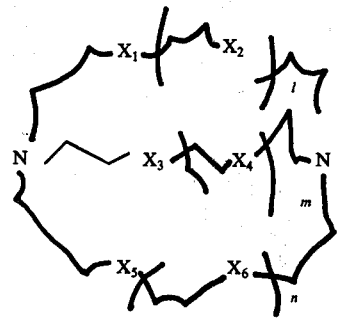

(wherein $l$, $m$ and $n$ are independently an integer of from 1 to 5, and $X_1$, $X_2$, $X_3$, $X_4$, $X_5$ and $X_6$ are independently O, S or R-N (in which R represents an alkyl group containing from 1 to 5 carbon atoms). Examples of the cryptate compounds include 4, 7, 13, 16, 21, 24-hexaoxy-1, 10-diazabicyclo [8, 8, 8] hexacosane, 4, 7, 13, 16, 21-pentaoxan-1, 10-diazabicyclo [8, 8, 5] tricosane, 4, 7, 13, 18-tetraoxa-1, 10-diazabicyclo [8, 5, 5] eicosane, and the like. The crown ethers and the compounds of the above general formula can be prepared by a known method as described in the above-mentioned literature.

In the practice of the invention, the oligomerization reaction is generally effected in a solvent under a normal pressure or a slightly elevated pressure at a temperature of 20° to 200° C, preferably 60° to 100° C, though the reaction pressure and temperature conditions may vary depending on the kind of an employed catalyst, the kind of solvent, and the composition of the desired oligomer product and so forth. The solvents useful in the practice of the invention include, for example, non-protolytic polar solvents such as N,N-dimethyl-formamide, N,N-dimethylacetamide, dimethylsulfoxide, acetonitrile, etc., and non-polar solvents such as hydrocarbons including dichloroethylene, 1, 1, 1-trichloroethane, 1, 1, 2-trichloroethane, 1, 2, 2-trifluoroethane, etc., glymes including mono-, di-, tri- and tetraethylene glycol dimethyl ether, and ethers such as diethyl ether, tetrahydrofuran, dioxane, etc., though almost all of organic solvents which are inert when placed under the oligomerization reaction conditions may be used in the oligomerization reaction according to the invention. Of these, N,N-dimethylformamide, N,N-dimethylacetamide and dimethylsulfoxide are preferable. In general, the rate of reaction and the composition of oligomer product are influenced to a certain extent by the kind of solvent, so that the solvent is preferred to be properly used.

The oligomerization reaction may be effected in a continuous or batch-wise manner. The concentration of the fluoride compound is desired to be greater than 0.01 mol/l of solvent and that of the crown ether greater than 1/50 mols of the employed fluoride compound. When the concentration of the fluoride compound is in the range of 0.1 to 1 mol/l, there is a tendency that higher the concentration, the oligomerization reaction proceeds under milder reaction conditions with a greater yield.

In some cases, use of a radical polymerization inhibitor such as α-pinene is effective in increasing an yield of oligomers. The radical polymerization inhibitor may be used in an ordinary small amount.

In general, the oligomerization reaction of tetrafluoroethylene results in formation of dimer through octamer, among which pentamer can be produced in an amount of about 50 to 60% or more.

If the oligomerization reaction is conducted in the presence of potassium fluoride alone without use of a crown ether, the reaction temperature is required to be above 100° C, with a selectivity to oligomers of as low as about 30 to 40%. In addition, the resulting oligomers are colored to a considerable extent due to decomposition of solvent under such high temperature conditions. In contrast, according to the process of the invention, the oligomerization reaction proceeds rapidly even at a temperature of about 80° C and the selectively to oligomers reaches as high as 55–100%, with reduced degree of coloration of the produced oligomers.

The fluoride compound-crown ether complex may be produced without resorting to any special reaction techniques. That is, it will suffice to add to the reaction system predetermined amounts of a fluoride compound and a crown ether with agitation. If necessary, a fluoride compound and a crown ether may be mixed with each other in a separate reactor to prepare crystals of a complex thereof for addition to the reaction system.

The present invention will be particularly illustrated by way of the following examples, in which percentages are by weight.

EXAMPLE 1

In a 200 cc electromagnetically agitated autoclave were placed 80 cc of N, N-dimethylformamide (DMF), 0.017 mols of dry potassium fluoride, 0.006 mols of 18-crown-6 and 0.0003 mols of α-pinene, and then the autoclave was hermetically sealed, followed by cooling with liquid nitrogen to solidify the content and degassing. Thereafter, 0.25 mols of tetrafluoroethylene was introduced into the autoclave while agitating, and the autoclave was again hermetically sealed. The content was gradually heated for oligomerization reaction to 75° C for 5 hours under agitation. The pressure in the autoclave was reduced from 20 kg/cm$^2$ guage to 7 kg/cm$^2$ gauge during a time period of from commencement of the reaction at 75° C till completion of the reaction. After completion of the reaction, the liquid content was weighed and the conversion of tetrafluoroethylene was calculated on the basis of the weight increment. Then, the content was transferred to a separating funnel to separate an oligomer layer therefrom, followed by measuring its weight. The thus separated oligomer was subjected to a gas chromatographic analysis, revealing that the conversion of the tetrafluoroethylene reached 60.4% and the selectivity to oligomers was 64.9%. It was also revealed that 58.6% of the oligomer product was a pentamer.

EXAMPLES 2-8

The general procedure used in these examples were similar to that described in Example 1 but the oligomerization reaction was effected using such reaction conditions, catalysts and solvents as shown in Table. The experimental results are also shown in Table below.

Table

| Ex. No. | potassium fluoride (mol) | crown ether*1 kind | amount by mol | reaction temperature (° C) | reaction time (hr) | conversion of tetrafluoroethylene (wt %) | selectivity to oligomers (wt %) | selectivity to pentamer (wt %) | solvent used |
|---|---|---|---|---|---|---|---|---|---|
| 2 | 0.017 | 18-crown-6 | 0.006 | 75 | 3.0 | 45.6 | 58.0 | 50.5 | N,N-dimethyl-acetoamide |
| 3 | 0.017 | DB18-crown-6 | 0.009 | 83 | 4.0 | 69.1 | 69.8 | 59.9 | N-N-dimethyl-formamide |
| 4 | 0.017 | " | 0.009 | 85 | 16.0 | 81.3 | 66.5 | 66.5 | " |
| 5 | 0.034 | " | 0.017 | 75 | 4.0 | 42.6 | 100.0 | 58.7 | " |
| 6 | 0.017 | B15-crown-5 | 0.009 | 100 | 4.0 | 79.7 | 45.5 | 59.7 | " |
| 7 | 0.013 | DB24-crown-8 | 0.0045 | 110 | 3.5 | 72.3 | 42.2 | 51.0 | " |

Table-continued

| Ex. No. | potassium fluoride (mol) | crown ether[1] kind | amount by mol | reaction temperature (°C) | reaction time (hr) | conversion of tetrafluoroethylene (wt %) | selectivity to oligomers (wt %) | selectivity to pentamer (wt %) | solvent used |
|---|---|---|---|---|---|---|---|---|---|
| 8 | 0.017 | DB18-crown-6 | 0.006 | 77 | 3.5 | 58.9 | 76.9 | 60.7 | dimethylsulfoxide |

[1]B15-crown-5: 23-benzo-1, 4, 7, 10, 13-pentaoxycyclopentadeca-2-en
18-crown-6: 1, 4, 7, 10, 13, 16-hyxaoxacyclooctadecane
DB18-crown-6: 2, 3, 11, 12-dibenzo-1, 4, 7, 10, 13, 16-hexaoxacyclooctadeca-2, 11-dien
DB24-crown-8: 2, 3, 14, 15-dibenzo-1, 4, 7, 10, 13, 16, 19, 22-octaoxacyclotetracosa-2, 14-dien In all of the above examples except Example 7, there were used 80 cc of solvent, 0.0003 mols of α-pinene and 0.25 mols of tetrafluoroethylene.

In Example 7, 60 cc of solvent, 0.0002 mols α-pinene and 0.16 mols of tetrafluoroethylene were used.

COMPARATIVE EXAMPLE 1

Example 1 was repeated using a reaction temperature of 100° C, a reaction time of 3.5 hours and 0.034 mols of dry potassium fluoride without use of a crown ether. During the course of the reaction, the reaction pressure in the autoclave was reduced from 23 kg/cm² gauge to 7 kg/cm² gauge. As a result of the gas-chromatographic analysis of the resulting oligomer product, it was found that the conversion of tetrafluoroethylene was 65.9% and the selectivity to the oligomers was 43.5%. Further, the selectivity to pentamer was found to be 57.3%. It will be understood from the above that the conversion and yield are both lowered when the oligomerization reaction is conducted without use of a crown ether even under conditions of elevated reaction temperatures and an increased amount of potassium fluoride catalyst.

COMPARATIVE EXAMPLE 2

Comparative Example 1 was repeated using a reaction temperature of 125° C and a reaction time of 2.5 hours. During the course of the reaction, the reaction pressure was changed from 23 kg/cm² gauge to 4 kg/cm² gauge. As a result of a gas-chromatographic analysis, it was revealed that the conversion of tetrafluoroethylene was 82.7% and the selectivity to oligomers was 37.3%. Further, the selectivity to pentamer or the content of pentamer in the oligomers was 51.8%. From the above results, it will be understood that the conversion increases but the selectivity decreases, lowering the yield of the oligomers as a whole.

COMPARATIVE EXAMPLE 3

A solution of 0.05 mols of tetramethylammonium chloride in 12 cc of methanol was dropped into a solution of 0.05 mols of potassium fluoride in 40 cc of methanol while agitating at room temperature in a stream of nitrogen. 1 minute after completion of the dropping, the resulting white precipitate was separated by filtration. To the filtrate was added 83 cc of N, N-dimethylformamide to completely distil off the methanol under conditions of 60°-70° C and 10-15 mmHg. Potassium chloride which had been precipitated upon adding the dimethylformamide was removed by filtration to obtain an N, N-dimethylformamide solution of tetramethylammonium fluoride.

Then, Example 1 was repeated using 80 cc of the thus obtained N, N-dimethylformamide solution of tetramethylammonium fluoride (0.022 moles) and reaction conditions of a reaction temperature of 60° C and a reaction time of 5.0 hours. As a result, the conversion of tetrafluoroethylene was 72.9%, the selectivity to oligomers 69.5% and the selectivity to pentamer was 57.2%.

COMPARATIVE EXAMPLE 4

Example 1 was repeated using 80 cc of the N, N-dimethylformamide solution of tetramethylammonium fluoride (0.017 mols) as prepared in Comparative Example 3 and the reaction conditions of a reaction temperature of 65°-75° C and a reaction time of 4.5 hours. As a result, the conversion of tetrafluoroethylene was 58.8%, the selectivities to oligomers and to pentamer were 66.5% and 61.4%, respectively.

What is claimed is:

1. A process for preparing oligomers of tetrafluoroethylene comprising subjecting tetrafluoroethylene monomer to an oligomerization reaction in the presence of a fluoride compound selected from the group consisting of potassium fluoride, sodium fluoride, cesium fluoride, ammonium fluoride, and a quaternary ammonium fluoride and a crown ether, at a temperature of about from 20° to 200° C, said oligomerization reaction being carried out in an organic solvent which is inert under said reaction conditions, said fluoride compound being employed in an amount greater than 0.01 mol per liter of said solvent and said crown ether being employed in an amount greater than 1/50 mol of the employed fluoride compound.

2. The process of claim 1 wherein the fluoride compound is potassium fluoride.

3. The process of claim 1 wherein the fluoride compound is sodium fluoride.

4. The process of claim 1 wherein the fluoride compound is cesium fluoride.

5. The process of claim 1 wherein the fluoride compound is ammonium fluoride.

6. The process of claim 1 wherein the fluoride compound is a quaternary ammonium fluoride.

7. The process of claim 1 wherein the crown ether is an 18-crown-6 compound.

8. The process of claim 7 wherein the crown ether is 18-crown-6.

9. The process of claim 7 wherein the crown ether is dibenzo-18-crown-6.

10. The process of claim 7 wherein the crown ether is dicyclohexyl-18-crown-6.

11. The process of claim 1 wherein the fluoride compound is potassium fluoride and the crown ether is an 18-crown-6 compound.

12. The process of claim 1 wherein said fluoride compound and said crown ether is in the form of a complex.

13. The process of claim 1 wherein the organic solvent is a member selected from the group consisting of N,N-dimethylformamide, N,N-dimethylacetamide, dimethylsulfoxide, acetonitrile, dichloroethylene, 1,1,1-trichloroethane, 1,1,2-trichloroethane, 1,2,2-trifluoroethane, mono-, di-, tri- and tetra-ethylene glycol dimethyl ether, diethyl ether, tetrahydrofuran, and dioxane.

14. The process of claim 13 wherein the organic solvent is N,N-dimethylformamide.

15. The process of claim 13 wherein the organic solvent is N,N-dimethylacetamide.

16. The process of claim 13 wherein the organic solvent is dimethylsulfoxide.

17. The process of claim 1 wherein the reaction temperature is in the range of about from 60° to 100° C.

18. The process of claim 1 wherein the reaction mixture also contains a small amount of α-pinene.

19. The process of claim 1 wherein a large proportion of the oligomers resulting from the oligomerization reaction contain at least four carbon atoms.

* * * * *